US008273579B2

(12) United States Patent
Morrison

(10) Patent No.: US 8,273,579 B2
(45) Date of Patent: Sep. 25, 2012

(54) METHOD AND APPARATUS FOR INSPECTING BIOLOGICAL SAMPLES

(75) Inventor: Allan D. Morrison, Acacia Ridge (AU)

(73) Assignee: Bizpac (Australia) Pty. Ltd., Acacia Ridge (AU)

( * ) Notice: Subject to any disclaimer, the term of this patent is extended or adjusted under 35 U.S.C. 154(b) by 1220 days.

(21) Appl. No.: 11/148,094

(22) Filed: Jun. 8, 2005

(65) Prior Publication Data

US 2005/0287678 A1     Dec. 29, 2005

(30) Foreign Application Priority Data

Jun. 8, 2004   (AU) ................................ 2004903077

(51) Int. Cl.
*G01N 21/00*     (2006.01)
*G01N 21/75*     (2006.01)
*G01N 33/48*     (2006.01)
*G01J 4/00*     (2006.01)

(52) U.S. Cl. ........ 436/164; 422/82.05; 356/39; 356/369
(58) Field of Classification Search .................. 436/164; 422/82.05
See application file for complete search history.

(56) References Cited

U.S. PATENT DOCUMENTS

| | | | | |
|---|---|---|---|---|
| 5,460,057 A | * | 10/1995 | Ostrup | 73/864.81 |
| 5,494,829 A | * | 2/1996 | Sandstrom et al. | 436/518 |
| 5,638,170 A | | 6/1997 | Trinka et al. | 356/244 |
| 5,641,682 A | * | 6/1997 | Pagels et al. | 436/43 |
| 5,770,389 A | * | 6/1998 | Ching et al. | 435/7.92 |
| 5,789,255 A | * | 8/1998 | Yu | 436/95 |
| 6,441,902 B1 | * | 8/2002 | Hilfiker et al. | 356/369 |
| 6,879,399 B2 | * | 4/2005 | Yamauchi | 356/344 |
| 2002/0137096 A1 | * | 9/2002 | Fodor et al. | 435/7.1 |
| 2004/0038413 A1 | * | 2/2004 | Kramer | 436/63 |
| 2004/0126281 A1 | | 7/2004 | Morrison | 422/58 |
| 2005/0129579 A1 | | 6/2005 | Morrison | 422/101 |

* cited by examiner

*Primary Examiner* — In Suk Bullock
*Assistant Examiner* — Bryan Kilpatrick
(74) *Attorney, Agent, or Firm* — Fulbright & Jaworski L.L.P.

(57) ABSTRACT

A method of selecting for analysis a sample of a biological material anisotropically distributed on a substrate, said method comprising the steps of directing a beam of radiation onto said substrate, said radiation being selected to interact with said anisotropically distributed biological material to an extent corresponding to said anisotropy; measuring said interaction at plurality of locations on said substrate; and selecting said sample by reference to said measurements.

An inspection apparatus for selecting for analysis a sample of a biological material anisotropically distributed on a substrate is also disclosed. The apparatus comprises a source of radiation selected to direct a beam of radiation onto said substrate, said radiation being selected to interact with said anisotropically distributed biological material to an extent corresponding to said anisotropy; a detector for measuring said interaction at plurality of locations on said substrate; and a processor coupled to the detector for utilizing the measurement at each of said plurality of locations to select a portion of said sample for further analysis.

13 Claims, 5 Drawing Sheets

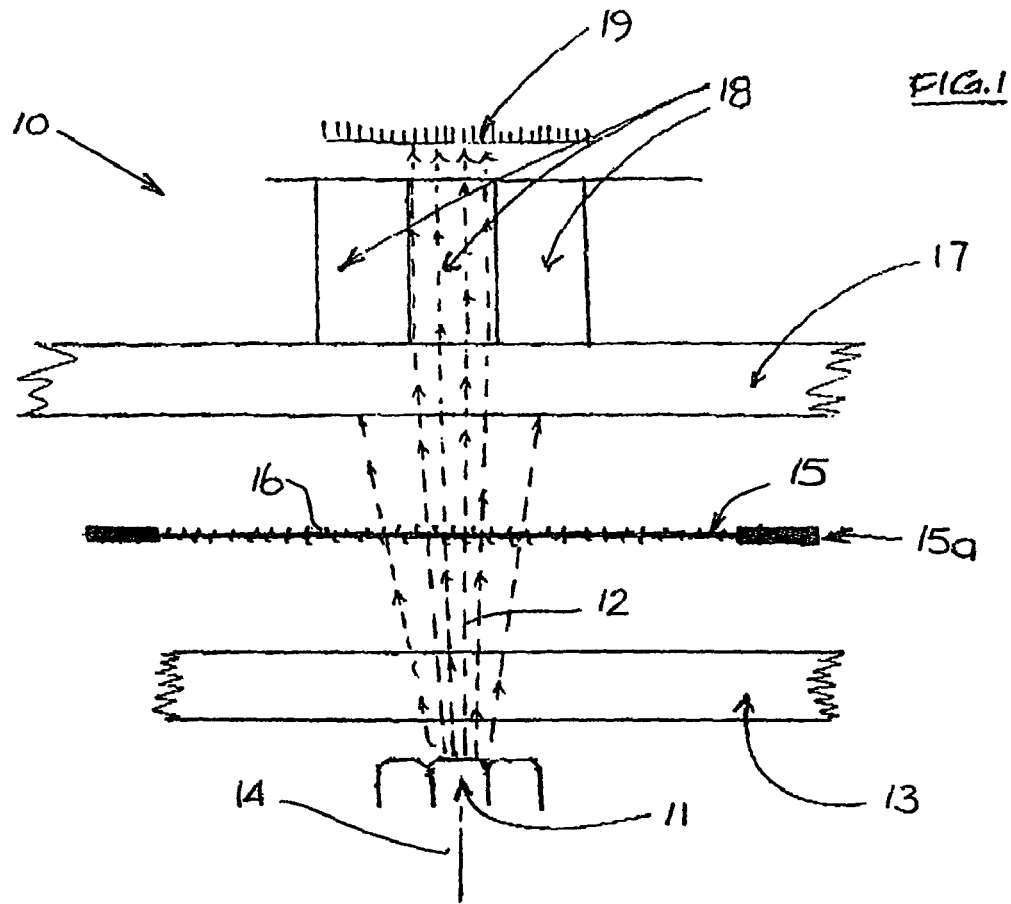
FIG.1
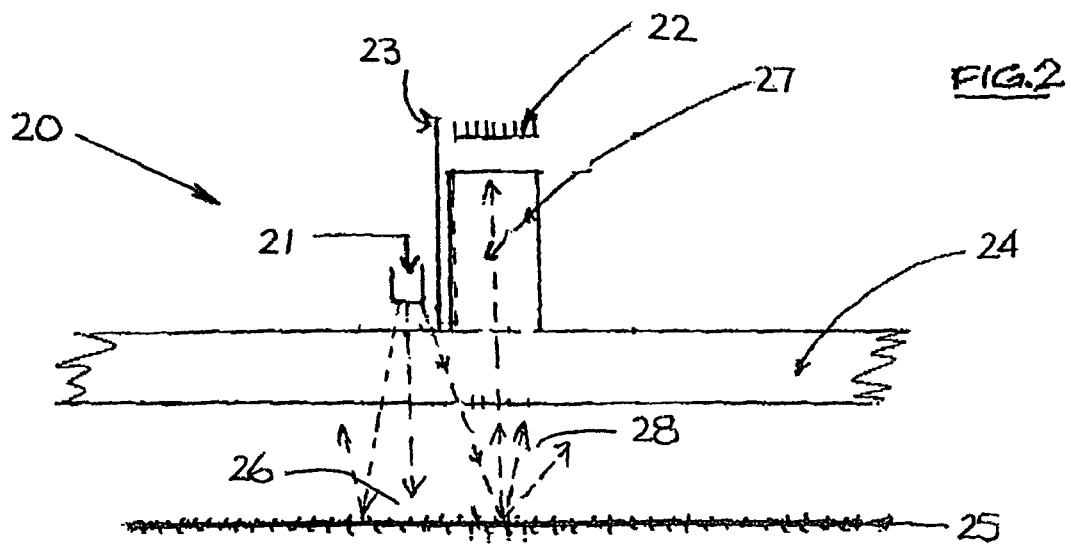
FIG.2
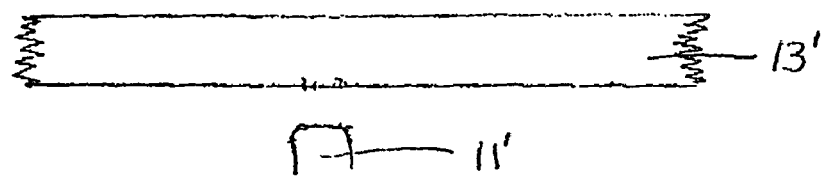

METHOD AND APPARATUS FOR INSPECTING BIOLOGICAL SAMPLES

CROSS-REFERENCE TO RELATED APPLICATIONS

This application claims the benefit of Australian Provisional Patent Application No. 2004903077, filed Jun. 8, 2004, which is hereby incorporated by reference in its entirety.

BACKGROUND OF THE INVENTION

1. Field of the Invention

The present invention relates to a method and apparatus for inspecting biological samples. This invention has particular application to the automated inspection of material prior to sampling for analysis purposes, and for illustrative purposes the invention will be further described with reference to this application. However, it is envisaged that this invention will find use in other applications, such as for sample identification, sample integrity assessment.

In particular, although not exclusively, the invention relates to a method of inspection of biological samples for selecting a portion of each sample for further analysis, and to an inspection apparatus for carrying out the method.

2. Discussion of the Background Art

Biological samples are often collected on absorbent media such as filter paper. Materials that have been collected and retained on a medium may need to be subject to several analyses, sometimes after storage for extended periods. Typically, portions of an original sample of material are periodically removed from the medium for analysis, such as an assay. Furthermore, the original sample may not be deposited evenly over the media, such as may occur during manual collection. Biological samples such as blood and other anisotropic materials may undergo some partitioning as a consequence of selective adsorption by the medium (such as migration of plasma away from the pigment).

It is important, if an analytical test is to be valid, that the portion subject to assay is either representative of the whole sample, or is selected to be the best part of a variable sample. However, if the sample is not homogeneously deposited on the media, the testing of some small portions of the sample may give different results to the testing of other small portions.

It may be equally important that sufficient sample material from the sample deposited on the media is tested.

In taking a sample for analysis, a typical method includes a small portion of the sample to be tested being punched out of filter paper on which the specimen is absorbed by a circular punch, resulting in one or more circular sample disks with diameter of between 1.2 mm and 6 mm.

SUMMARY OF THE INVENTION

Object of the Invention

Pursuant to the above discussion it is desirable that the most appropriate part of the sample is chosen in order to provide the most accurate results. There is accordingly a need for a method and apparatus for inspection of biological samples for selecting a portion of each sample for further analysis.

Disclosure of the Invention

In one broad form, the present invention resides in a method of selecting for analysis a sample of a biological material anisotropically distributed on a substrate and including the steps of:

directing a beam of radiation onto said substrate, said radiation being selected to interact with said anisotropically distributed biological material to an extent corresponding to said anisotropy;

measuring said interaction at plurality of locations on said substrate; and selecting said sample by reference to said measurements.

As used herein the expression "anisotropically distributed" refers to the biological material being anisotropically distributed over the substrate by virtue of an inherent anisotropy of application to the substrate and by virtue of partitioning as a consequence of selective adsorption of the biological material by the substrate.

The radiation may be selected for its absorptive, transmissive or reflective interaction with the anisotropically distributed biological material. For example, for selecting a sample of a blood specimen, the radiation may comprise a source of red light, wherein the interaction may be with the haem iron complexes of the material. Preferably the radiation is in the electromagnetic spectrum (EMR), although it is envisaged that the present invention may utilize other forms of radiation such as particle radiation. The EMR radiation may be in the visible spectrum. However, it is equally open that the UV/VIS, IR and high-energy (X- and γ-) radiation may find utility in the method of the present invention. The radiation may be coherent radiation such as laser light or may have a significant dispersion. The radiation may be monochromatic or may comprise a spectrum of a selected band width.

The radiation source may comprise any light emitting element such as a light emitting diode or filament source. In the case of polychromatic sources the frequency or bandwidth may be provided by any suitable means such as a filter, grating or other monochromator. Alternatively the bandwidth or frequency reaching the detector may be selected by filter, grating or other monochromator after interaction with the sample. For example, for selection of samples for analysis from blood absorbed on filter paper the source may comprise a LED of median or notional wavelength of emission of 636 nm.

The measurement may be by any suitable means determined by the choice of radiation and the nature of the interaction with the sample. For example, in the case of a blood specimen absorbed onto filter paper or the like, the measurement may be by means of a detector of the reflected or transmitted spectrum of an incident light source. Transmission through the specimen and substrate of light from the aforementioned LED may be detected by, for example a photodiode responding to a suitable wavelength. Available photodiodes for example may have a notional response of 700 nm, distributed between 400 nm to 870 nm.

The measuring of the interaction at a plurality of locations on the substrate may be achieved by any number of means. For example, the substrate may be evenly illuminated and the plurality of locations scanned by a scanning detector of transmission or reflection as the case may be. The illumination may also be by a single point source which is scanned over the substrate in register with the scanning detector. For reflective measurement the point source and the detector may be integrated in the same device.

Alternatively the measuring may comprise the use of an array of sources each element of which is associated with a discrete detector. The array may comprise a 2 dimensional array covering the whole field. Alternatively the array may comprise a linear array adapted to be mechanically or optically scanned over the substrate.

In a yet further example there may be provided a single source providing a pixellated incident radiation by means of a shadow mask or the like, and the detection being by means of multiple detectors in register with the shadow mask or by a scanning detector.

The radiation and the detection may be quantized to pixels of a size corresponding to the sample size to be punched out of the substrate for analysis. In this case the measure is of the average interaction between the radiation and the biological material over the sample area. Alternatively the radiation and detection may effect a quantization at much smaller scales in order to optimize the sample selection.

The substrate may be analysed from one or both sides. This may be used to confirm that the sample material had penetrated through both sides of the substrate, thus providing additions data in support of a sampling decision, particularly where the analysis after sampling is a quantitative extraction. This type of assessment is currently employed in laboratories, where laboratory technicians visually inspect both sides of the cards in an attempt to identify the common area on both sides where sample material is evident to the naked eye. Detectors could be positioned to receive light reflected off each side of the card. Where this reflected light approach was also to be used in conjunction with the approach of passing light through the filter paper card, measuring both the transmitted light and the reflected light so as to identify suitable portions of the sample might be performed consecutively.

The detected measurement for each location may be in the form of an analogue or digital signal depending on the nature of the detector. In certain embodiments of the present invention an analogue signal from each location is converted into a digital signal, although it is envisaged that the data may remain analogue.

The measurements from the respective positions may be utilized in many ways. For example, the respective signals may be used to generate a three dimensional array of measurements where the X and Y directions of the array correspond to the 2 dimensional surface of the substrate and the Z direction corresponds to the measurement at each location. In the case of fine-resolution apparatus this may be represented as a smooth topographic surface. In the interests of reducing processing requirements, the plot may be generated digitally as more or less points on the surface with digital smoothing.

The data output may provide a readable plot that can direct an operator to the potential sample site for manual extraction of the sample. Alternatively, the signals may be integrated by processing to form an output that factors the sample size to direct automated sampling apparatus to take the sample.

In a further broad form there is provided an apparatus for selecting for analysis a sample of a biological material anisotropically distributed on a substrate, said apparatus including:
  a source of radiation selected to direct a beam of radiation onto said substrate, said radiation being selected to interact with said anisotropically distributed biological material to an extent corresponding to said anisotropy;
  a detector for measuring said interaction at plurality of locations on said substrate; and
  a processor coupled to the detector for utilising the measurement at each of said plurality of locations to select a portion of said sample for further analysis.

Suitably the source of radiation is a light source and the detector measures the intensity of light. Preferably the light source takes the form of an array of light emitting diodes (LEDs). Suitably the detector is a photo-electric device, capable of measuring the intensity of light incident at a plurality of pixels, and measurements are made at a plurality of predetermined locations, corresponding to said respective pixels.

A lens or similar focussing arrangement may be provided for focussing reflected or transmitted radiation onto the detector.

If required, a director is provided for directing the electromagnetic radiation emanating from said source. The director may take the form of an aperture, a series of mirrors and/or an optical fibre through which electromagnetic radiation is passed prior to impinging on the media. In the case of an aperture, its size may corresponding to a desired size or area of said portion of the sample.

Preferably the radiation director and the detector are fixed to a common support member that is movable relative to the media. Most preferably, the support member has a substantially C-shaped section wherein the light source and/or director and the light detector are fixed to respective opposing ends of the C section.

In an alternative arrangement, the light source and/or director and the light detector are located adjacent to one another on the support member, whereby light reflected from an obverse face of the media may be detected.

Suitably the detector is placed adjacent to a reverse face of the media, preferably disposed opposite to the direction of the electromagnetic radiation incident on said obverse face of the media.

If required, the inspection apparatus may be co-located with a sampling apparatus for removing said portion of the sample from the media, preferably on a support member for a punching head and die.

The apparatus may further include a further light source disposed in lateral relation with said detector, whereby light reflected from the sample may be measured. A light barrier is suitably placed between the light source and the adjacent detector.

BRIEF DETAILS OF THE DRAWINGS

In order that this invention may be more readily understood and put into practical effect, reference will now be made to the accompanying drawings illustrate preferred embodiments of the invention, and wherein:

FIG. 1 is a decomposed side elevational view of an inspection apparatus of a first embodiment of the present invention;

FIG. 2 is a decomposed side elevational view of an inspection apparatus of a second embodiment of the present invention;

DESCRIPTION OF EMBODIMENTS OF THE INVENTION

Figure 6:
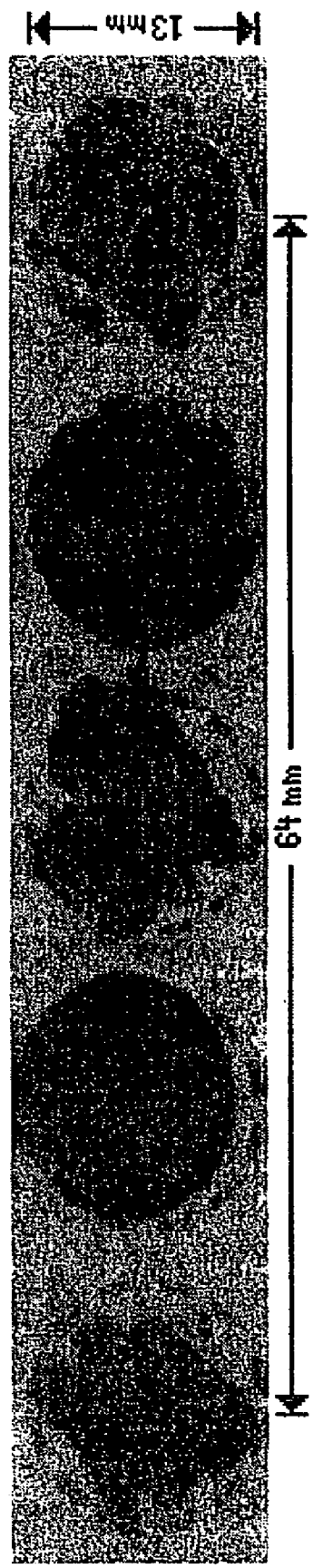
FIG. 6 is a representation of a typical biological specimen for analysis.

A typical blood-spot specimen for sampling is illustrated in the photographic representation of FIG. 6. As can be seen the blood spots are absorbed onto a filter paper substrate. What can be seen by the eye is that the blood spots are of variable extent and regularity. Superimposed on the specimen are the dotted outlines of typical punching sizes over each blood spot. It can be seen that the first, third and fifth spots do not occupy the punching field and are intuitively unlikely to for a representative sample. The second spot from left would be prima facie representative if it were indexed accurately with the punch. The fourth from right is what would appear to be an ideal spot for analysis.

However, the question remains as to which of the spots is actually providing the best sample, given the anisotropy of the absorbed material. Accordingly one may expect that fourth from right is an ideal spot for analysis, but analysis at a representative frequency may indicate that a different spot is better.

FIG. 1 illustrates an inspection apparatus 10 of a first embodiment which includes a light source 11 in the form of high intensity light emitting diodes (LEDs). The LEDs are suitably chosen such that the light 12 should not deflect by more than about 30° from the emitting axis 14 of the LEDs. The light 12 is passed through a transparent protective cover 13, such as glass window, which protects the LEDs from dust and other adverse environmental conditions. At least one sample 16 of biological material for inspection, which is carried on media 15 such as a paper filter card, is placed in the path of the light 12. In a preferred arrangement, an array of approximately thirty (30) high intensity LEDs are mounted in a single row beneath the media 15, which media supported by a peripheral frame 15a. The individual LEDs effectively direct the light from the light source onto the media 15 carrying the sample(s) 16 of biological material.

The light passes through the media 15 and sample 16 before again passing through an opposing protective glass window 17. Immediately adjacent to the opposing glass window 17 is a lens 18, being one of an array of similar lenses, which focuses the light that has passed through the sample 16 parallel to the axis of the lens. The light passes through the lens 18 to an array of radiation detectors 19, whereby the light intensity is registered at a plurality of locations on a pixel-by-pixel basis.

Each pixel of the detector array 19, suitably of the photo-electric type, produces an analogue voltage proportional to the intensity/time of light exposure. The analogue voltage can be directed to an analogue-to-digital conversion circuitry to produce a gray scale image for further processing in a processor (not shown).

The lens 18 is arranged to produce a unit-magnification image from the surface of the filter card 15 to the detector 19. The image area is an array of approximately 2 mm diameter discs of light overlapping each other for the length of the lens 18. Each pixel suitably measures approximately 63.5×55.5 µm on 63.5 um centre spacings and the array is 1280×1 pixels in dimension. The total width of the scan will be around 81 mm in the embodiment; with the lens 18 being slightly wider than then detector array 19 to overcome edge effects.

FIG. 2 shows the operation of an inspection apparatus 20 of a second embodiment of the invention which employs a reflected light detection arrangement. In this embodiment, the light source 21 is arranged adjacent to, and on the same side of a sample, as the detector array 22. A light barrier 23, in the form of a lateral wall, is provided between an array of between twelve (12) and thirty (30) LEDs forming the light source 21 and the detectors 22. The source 21 transmits light through a transparent cover 24, such as a glass window, onto the media 25 carrying the sample 26. Because the media 25, in this example a paper filter card, does not have a smooth surface, light is reflected off in all directions. Some of the light will strike the media 25 and will be reflected up into the array of lenses 27 and into the array of detectors 22, where the intensity of the reflected light is registered on a pixel-by-pixel basis.

It will be appreciated that the second embodiment may also optionally incorporate a further light source 11' provided on the reverse side of the media 25, in a similar arrangement to the light source depicted in FIG. 1. The further light source 11' will be able to selectively direct light through a window 13' and the sample 26 carried by the media 25. It will be appreciated that the array of LEDs 21 provided on the obverse side of the media 25 may be switched off when undertaking transmitted light measurements using further source 11', and vice-versa to selectively allow for reflected light measurement.

Either array of LEDs 21, 11' may be controlled such that the intensity of light output is modulated and the detector array can be varied in terms of the light integration time. The objective in measuring the amount of reflected light from the media 25 is to inspect for any distortions or inconsistencies in the surface of the media, which might also lead to the conclusion that the inspected portion of the sample 26 is not suitable for analysis.

In some instances the manner in which the sample is applied to the paper card may result in damage to the media. In some examples even though the passing of light through the media might suggest that it is suitable for analysis, on the basis of the density of sample material in the media, the sample may not in fact be suitable for analysis. Accordingly, simply passing light through the media 25 may give a misleading result. In these instances, the review of light intensity for candidate portions of the sample after passing through the media and the analysis of the consistency of the surface of the media, based on the pattern of light reflected from the surface of the media, will allow for a more comprehensive examination of the suitability of the sample.

Figure 3:
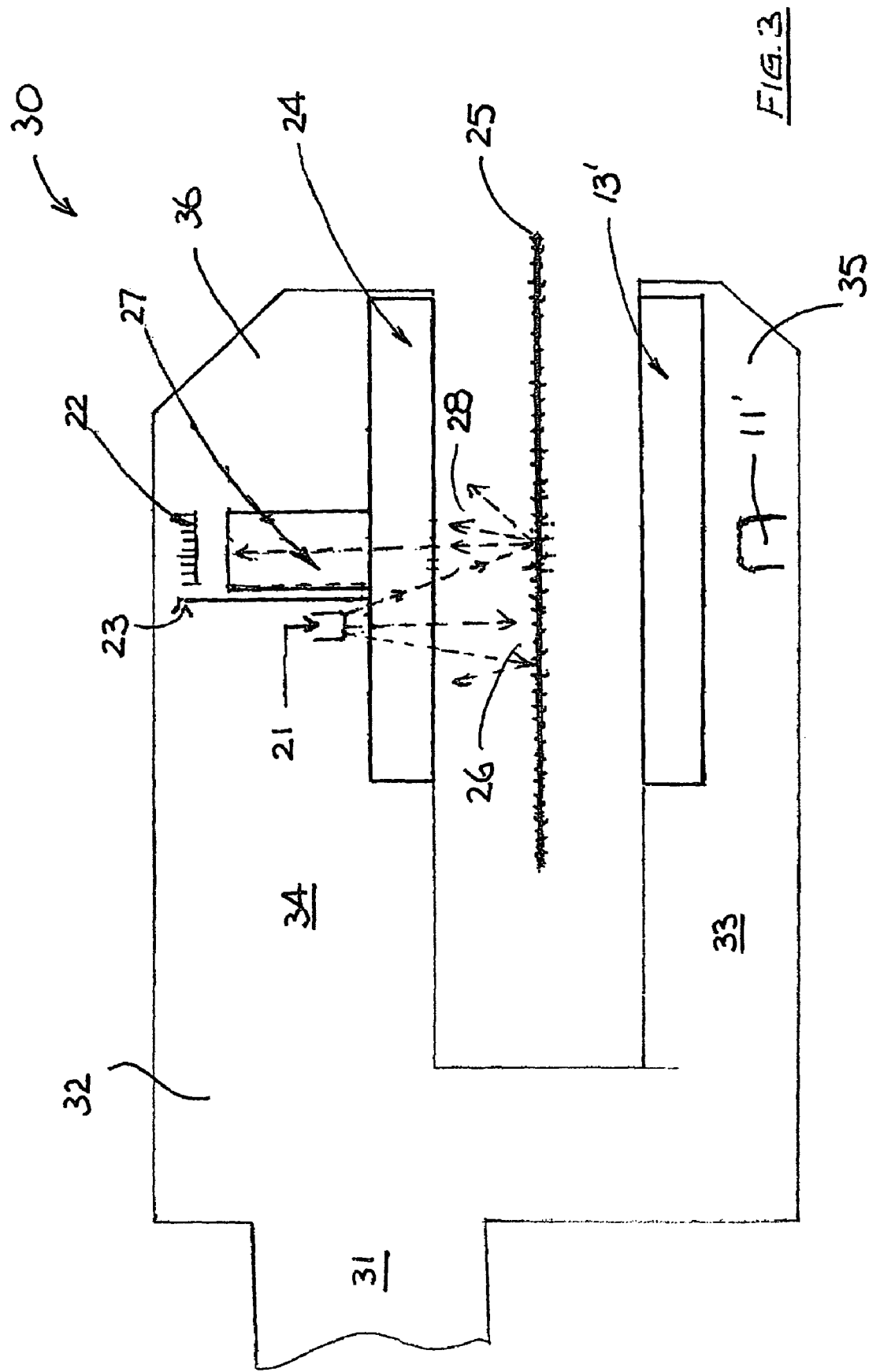
FIG. 3 is a side elevational view of an inspection apparatus of the second embodiment incorporated into a scanning head of the inspection apparatus.
Figure 4:
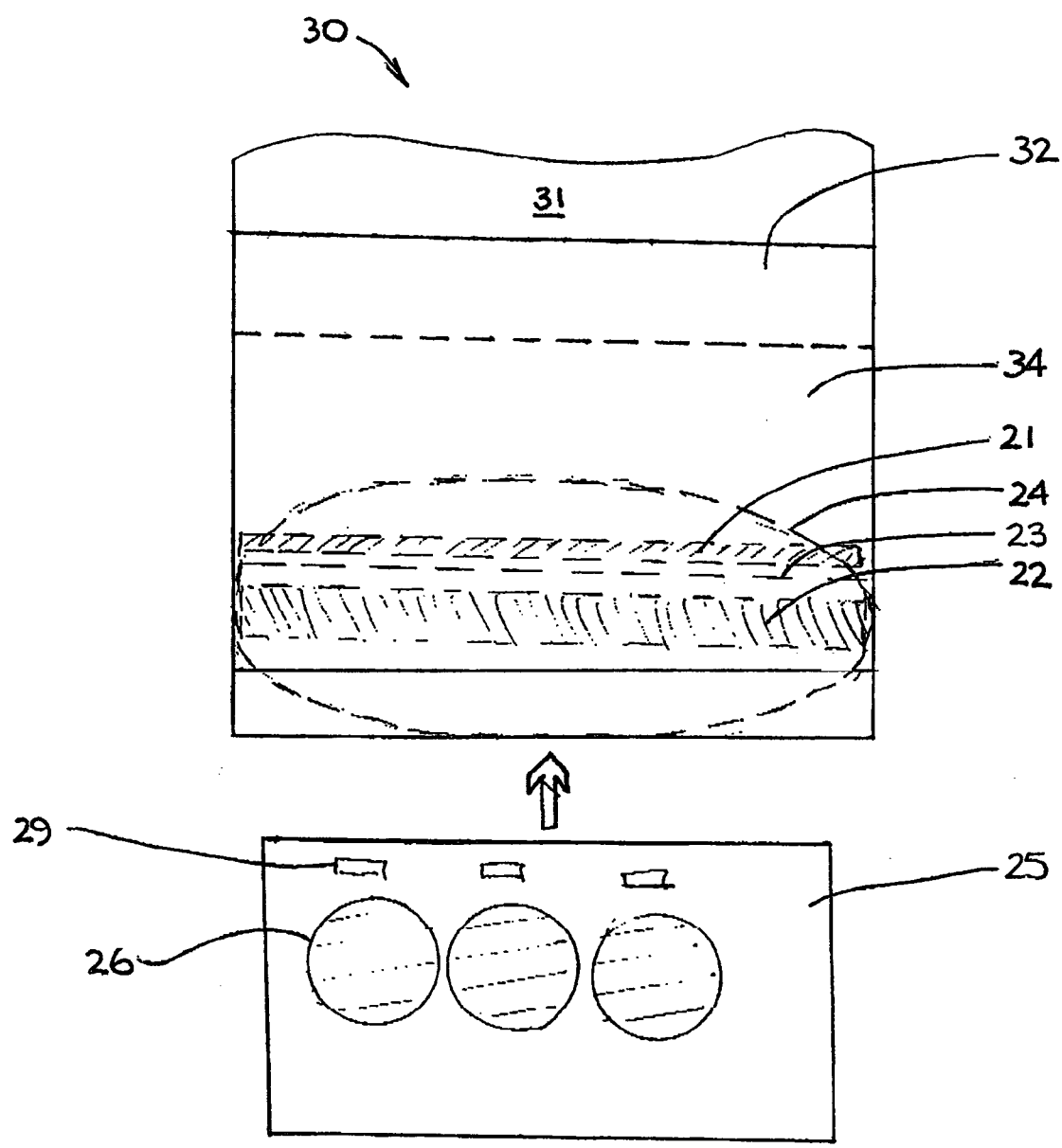
FIG. 4 is a sectional top plan view of the scanning head of the apparatus depicted in FIG. 3.

Referring now to FIGS. 3 and 4, there is shown a scanning head 30 with a support assembly 31 for the inspection apparatus 20 of the second embodiment. The support assembly is in the form of a substantially C-shaped member 32 having opposing arms 33, 34. The primary light source 11', suitably in the form of a linear array of LEDs and an associated glass window 13' is disposed in a free end 35 of the lower arm 33 of the C-shaped member 32. The detectors 22, lens 27 and associated glass window 24 is disposed in an opposing free end 36 of the upper arm 34 of the C-shaped member or C-section 32.

A medium in the form of a paper card 25 may be inserted either manually or automatically into the C-section 32 in a direction indicated by the arrow in FIG. 4. The card includes dried biological samples 26, such as blood, within designated areas on the card. The number of designated areas per card may vary, but preferably are in the range of 3-8, most preferably 4-6 inclusive. As the card 25 passes through the C-section and above the LEDs 11' of the primary light source (see FIG. 3), the LEDs pass light through the card and the samples 26, with that light being received through the lenses 27 and by the detectors 22.

The secondary light source 21 can be used as an alternative source to facilitate detection of light reflected from the medium 25, as required. The sample card 25 can also include, in one embodiment, checkboxes 29 associated with each sample area 26. In the event that the laboratory has itself observed any inadequacy of a sample—prior to scanning by the inspection apparatus 30—then the checkbox may be appropriately marked. The results of the scanning of the marked samples may then be discounted, so that no suitable punching sites or sample portions are identified from the whole sample area.

In embodiments where the movement of the card 25 into the C-section 32 is automated, as the card is inserted between the opposed arms 33, 34 the scanner may be used to detect the leading edge of the card 25. The detected card edge is suitably utilised as a reference point for the identification of all other locations on the card 25. With automation, the card 25 can then be inserted predetermined standard distances into the identification apparatus 30, as required to ensure that scanning only occurs in the checkbox area (if checkboxes are incorporated in the sample card), and in other sample areas on the card where it is most likely that the sample is located, thus speeding up the scanning process.

Figure 5:
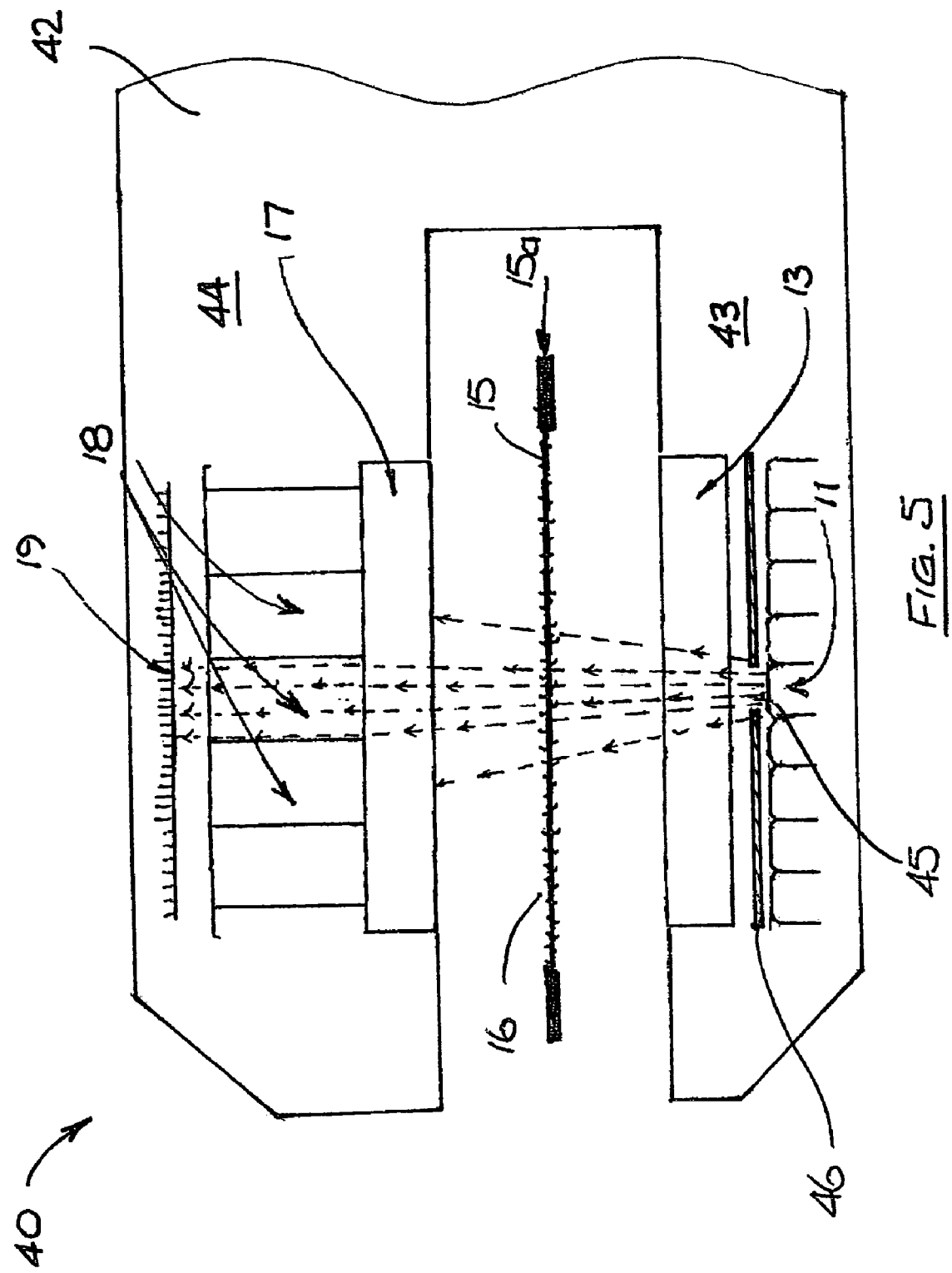
FIG. 5 is a side elevational view of an inspection apparatus of the first embodiment incorporated into a further scanning head.

FIG. 5 illustrates an alternative embodiment wherein a scanning head 40 is provided with a support assembly 41 for the inspection apparatus 10 of the first embodiment. The support assembly is again in the form of a substantially C-shaped member or C-section 42 having opposing arms 43, 44. In contrast to the embodiments shown in FIGS. 3 and 4 wherein the array of LEDs, lenses, and detectors are positioned on a line perpendicular to the arms of the C-section, these components are instead disposed along the arms of the C-section as shown.

The inspection apparatus includes a light source 11, in the form of an array of LEDs, mounted on a first arm 43 of the support assembly 42. A light director 46, such as an LCD shutter, selectively provides a circular aperture 45 through which light is passed before impinging on the sample 16. The aperture 45 of the embodiment has a diameter of 3.2 mm which corresponds to the size of a disc shaped portion desired to be removed from the sample 16 for analysis. The sample 16 is carried on media, again in the form of a filter paper card 15 disposed in a peripheral supporting frame 15a. The sample 16 may take the form of dried biological fluids, such as blood, urine or saliva.

The inspection apparatus further includes a light detector 19 for measuring the intensity of light that is transmitted through the sample 16 and paper media 15. The measurement represents the average intensity of the light across the diameter of the circular aperture 45 through which light is passed. In the above example where the desired diameter of the disc shaped portion is 3.2 mm, then the diameter of the circular aperture through which light is passed is suitably also 3.2 mm, such that the resulting measurement is of the average intensity of light across the area of the aperture.

In the present embodiment the detector 19, formed by an array of photo-electric cells, is located on the reverse side of the media to which the light impinges and opposite to the aperture 45 and light source 11. The support assembly 42 includes a substantially C-shaped member 40 having free ends 41 and 42. The light source and director are fixed to a first end 41 of the support member 40 and the detector 19 and associated array of lenses 18 is fixed to the second arm 44 in opposed relation to the source 11 and aperture 45.

It will be appreciated that the intensity of light measured after it passes through the media 15 where no sample is located is different to the intensity of light after is has passed through media where sample 16 is located. The sensitivity of light measurement can be adjusted, so that differences in the density of different samples can be recognized. In effect the measurement reflects the average density of sample across that circular area.

The C-shaped member 42 allows the frame 15a supporting the media 15 to pass between the light transmitting and sensing parts of the inspection apparatus 40. Either the media can be passed through the C-section, which is fixed, or the C-section can pass over the media, as required. Under either approach, the light emitting part can make sufficient passes over the media, targeting different candidate portions of the sample, to allow for a measurement of a plurality of portions on the media.

Where a laboratory wishes to introduce a protocol such that it does not wish a disc to be punched from a location within, for example 2 mm from the edge of the sample on the media, then the aperture diameter can be increased by twice that amount, in this case 4 mm, and the system will find a location where sample covers the required disk size plus an extra radius of 2 mm, thereby ensuring that the required disk is at least 2 mm from the edge of the sample. In this case, of course, the system measures the average density of the sample across the entire diameter of the scanned area, i.e. the required disk size plus 4 mm.

The inspection apparatus of the invention can be used to locate the sample on the media by any number of methods, including the following:

1. the apparatus can be used to locate the edge of the media in a number of places, and these can be used as reference points to locate the sample on the media which is generally deposited in designated areas; or
2. where the device is an integral part of a punch unit designed to punch holes in the media, then holes could be punched in a part of the media known to not contain sample, and the media can then be introduced to the scanner, which will be able to detect the location of the punched holes and use those holes as reference points for locating the sample.

In another embodiment of the invention, where the scanner device is an integral part of a sampling device including a punch and die unit for removing small portions of the sample of fixed size from the sample, then where particular small portions meet certain measurement parameters set for the scanning process, then those particular portions can be identified for the purpose of being punched from the sample.

Thus it will be appreciated that, in certain embodiments, the method and apparatus of the invention can be used for a number of different but related purposes, including determining:

a. the location of a sample on media such as a filter paper card (including those parts of the original sample not already removed from particular locations on the media);
b. the amount of sample on the media;
c. the homogeneity of the sample on the media;
d. the density of the sample on the media; and/or
e. the general suitability of the sample for use in assays or other processing.

It is to be understood that the above embodiments have been provided only by way of exemplification of this invention, and that further modifications and improvements thereto, as would be apparent to persons skilled in the relevant art, are deemed to fall within the broad scope and ambit of the present invention described herein and defined in the claims which follow.

I claim:

1. A method of selecting for analysis a sample of an anisotropically distributed material, the method comprising:

directing a beam of radiation onto a plurality of locations of an anisotropically distributed material in an absorptive substrate;

measuring an intensity of radiation transmitted through the anisotropically distributed material in an absorptive substrate at each of the plurality of locations;

comparing the intensity of radiation transmitted through the anisotropically distributed material in an absorptive substrate at each of the plurality of locations;

selecting one of the plurality of locations as a sample site based on a comparison of the intensity of radiation transmitted through the anisotropically distributed material in an absorptive substrate at each of the plurality of locations; and removing the sample site from the absorptive substrate.

2. The method of claim 1 wherein the intensity of radiation transmitted through the anisotropically distributed material in the absorptive substrate is measured at the plurality of locations on a pixel-by-pixel basis.

3. The method of claim 2 wherein the intensity of radiation transmitted through the anisotropically distributed material in the absorptive substrate is measured by a photo-electric detector.

4. The method of claim 3 wherein the photo-electric detector produces a voltage proportional to the intensity of the radiation.

5. The method of claim 3 further comprising focusing the radiation transmitted through the anisotropically distributed material with a lens between the absorptive substrate and the photo-electric detector.

6. The method of claim 1 wherein directing the beam of radiation comprises directing light from a light source.

7. The method of claim 6, further comprising measuring light reflected from the anisotropically distributed material at each of the plurality of locations.

8. The method of claim 7 further comprising analyzing the consistency of the light reflected from the anisotropically distributed material at each of the plurality of locations.

9. The method of claim 8 wherein selecting one of the plurality of locations as a sample site is also based on the consistency of the light reflected from the anisotropically distributed material at each of the plurality of locations.

10. The method of claim 6 wherein the light source is a high intensity LED.

11. The method of claim 5 wherein the beam of radiation is selected for its absorptive or transmissive interaction with the anisotropically distributed biological material.

12. The method of claim 5 wherein a photodiode is used to measure the intensity of radiation transmitted through the anisotropically distributed material.

13. The method of claim 5 wherein removing the sample site from the absorptive substrate comprises using a punch to remove a portion of the anisotropically distributed material in the absorptive substrate.

* * * * *